United States Patent [19]

Fabry

[11] Patent Number: 5,691,299
[45] Date of Patent: Nov. 25, 1997

[54] ANIONIC DETERGENT MIXTURES

[75] Inventor: Bernd Fabry, Korschenbroich, Germany

[73] Assignee: Henkel Corporation, Plymouth Meeting, Pa.

[21] Appl. No.: 569,811

[22] Filed: Dec. 8, 1995

[30] Foreign Application Priority Data

Dec. 8, 1994 [DE] Germany ............... 44 43 643.2

[51] Int. Cl.$^6$ ................. C11D 1/66; C11D 3/32
[52] U.S. Cl. ............ 510/501; 510/502; 510/505; 510/506
[58] Field of Search ............... 510/501, 502, 510/505, 506

[56] References Cited

U.S. PATENT DOCUMENTS

| | | | |
|---|---|---|---|
| 1,985,424 | 12/1934 | Piggott | 260/124 |
| 2,016,962 | 10/1935 | Flint | 260/127 |
| 2,703,798 | 4/1955 | Schwartz | 260/211 |
| 2,941,950 | 6/1960 | Korpi et al. | 510/502 |
| 5,500,150 | 3/1996 | Scheibel et al. | 510/502 |

FOREIGN PATENT DOCUMENTS

| | | |
|---|---|---|
| WO9206984 | 4/1992 | WIPO. |
| WO9412472 | 6/1994 | WIPO. |

OTHER PUBLICATIONS

Falbe(ed.), "Surfactants in Consumer Products", Springer Verlag, Berlin–Heidelberg, 1987, p. 61.

*Primary Examiner*—Margaret Medley
*Attorney, Agent, or Firm*—Wayne C. Jaeschke; John E. Drach; Real J. Grandmaison

[57] ABSTRACT

The invention relates to new anionic detergent mixtures obtained by reacting mixtures containing
(a) fatty acid-N-alkyl polyhydroxyalkylamides and
(b) fatty alcohols or fatty alcohol alkoxylates
with gaseous sulfur trioxide or chlorosulfonic acid in the absence of inert solvents and then neutralizing the reaction product with bases. The mixtures show excellent surface-active properties and are suitable for a number of applications.

20 Claims, No Drawings

ANIONIC DETERGENT MIXTURES

BACKGROUND OF THE INVENTION

1. Field of the Invention

This invention relates to anionic detergent mixtures obtainable by co-sulfation of fatty acid-N-alkyl polyhydroxyalkylamides and fatty alcohols or fatty alcohol alkoxylates, to a process for their production and to their use for the production of surface-active formulations.

2. Discussion of Related Art

Fatty acid-N-alkyl polyhydroxyalkylamides are nonionic surfactants which are obtained by reductive amination of sugars with primary amines and subsequent acylation of the aminosugars with fatty acid esters. Lauric acid or cocofatty acid N-methyl glucamides are preferably used in manual dishwashing detergents and liquid detergents.

However, besides a need for nonionic glucamides, there is a demand in the market place for correspondingly synthesized anionic compounds. The simplest way of converting a nonionic surfactant into an anionic surface-active compound is to sulfate hydroxyl groups present in the molecule. However, since the glucamides are derived from carbohydrates, the effect of sulfonating agents, for example oleum or sulfur trioxide, leads to very considerable oxidation of the sugar component and to intensive carbonization. To overcome this problem, it is proposed, for example, in WO 94/12472 (Procter & Gamble) to react fatty acid-N-alkyl glucamides with a complex of sulfur trioxide and pyridine in inert organic solvents, for example methylene chloride or pyridine. However, apart from the fact that the removal of pyridine is hardly so complete that the resulting products would not be affected by an aminic odor, the procedure involved is extremely complicated and is not suitable for implementation on an industrial scale.

Accordingly, the problem addressed by the present invention was to provide an improved process for the production of anionic derivatives of fatty acid-N-alkyl polyhydroxyalkylamides which would not be attended by any of the described disadvantages and which would provide light-colored products with excellent detergent properties.

DESCRIPTION OF THE INVENTION

The present invention relates to anionic detergent mixtures which are obtained by reacting mixtures containing (a) fatty acid-N-alkyl polyhydroxyalkylamides and
(b) fatty alcohols or fatty alcohol alkoxylates with gaseous sulfur trioxide in the absence of inert solvents and then neutralizing the reaction product with bases.

It has surprisingly been found that the use of fatty alcohols or alkylene oxide adducts thereof as non-inert solvents even allows the use of strong sulfating agents, such as sulfur trioxide or chlorosulfonic acid (CSA) for example, without any carbonization of the sugar occurring. In the course of the sulfation reaction, it is mainly the primary hydroxyl group of the fatty acid-N-alkyl polyhydroxyalkylamides which is sulfated. The "solvent" is also sulfated to substantially the same extent and converted into an anionic surfactant form. Accordingly, the resulting products are mixtures of sulfated fatty acid-N-alkyl polyhydroxyalkylamides on the one hand and fatty alcohol (ether) sulfates on the other hand. The ratio between the two products is of course dependent on the ratio in which they were used. Accordingly, the resulting anionic surfactant mixtures have a very small unsulfonated component and particularly high foaming power.

The present invention relates to a process for the production of anionic detergent mixtures in which mixtures containing (a) fatty acid-N-alkyl polyhydroxyalkylamides and
(b) fatty alcohols or fatty alcohol alkoxylates are reacted with gaseous sulfur trioxide in the absence of inert solvents and the reaction product obtained is neutralized with bases.

Fatty Acid-N-alkyl Glucamides

Fatty acid N-alkyl polyhydroxyalkylamides are known nonionic surfactants and correspond to formula (I):

in which $R^1CO$ is an aliphatic acyl radical containing 6 to 22 carbon atoms, $R^2$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups.

The fatty acid N-alkyl polyhydroxyalkylamides are surfactants which may normally be obtained by reductive amination of a reducing sugar with ammonia, an alkylamine or an alkanolamine and subsequent acylation with a fatty acid, a fatty acid alkyl ester or a fatty acid chloride. Processes for their production are described in U.S. Pat. No. 1,985,424, in U.S. Pat. No. 2,016,962 and in U.S. Pat. No. 2,703,798 and in International patent application WO 92/06984. An overview of this subject by H. Kelkenberg can be found in Tens. Surf. Der. 25, 8 (1988).

The fatty acid N-alkyl polyhydroxyalkylamides are preferably derived from reducing sugars containing 5 or 6 carbon atoms, more particularly from glucose. Accordingly, the preferred fatty acid N-alkyl polyhydroxyalkylamides are fatty acid N-alkyl glucamides which correspond to formula (II):

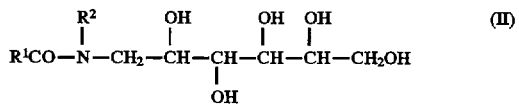

Preferred fatty acid N-alkyl polyhydroxyalkylamides are glucamides corresponding to formula (II) in which $R^2$ is hydrogen or an amine group and $R^1CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid N-alkyl glucamides (II) obtained by reductive amination of glucose with methylamine and subsequent acylation with lauric acid or $C_{12/14}$ coconut oil fatty acid or a corresponding derivative are particularly preferred. In addition, the polyhydroxyalkylamides may also be derived from maltose and palatinose.

Fatty Alcohols or Fatty Alcohol Alkoxylates

Component (b) is selected from fatty alcohols or fatty alcohol alkoxylates corresponding to formula (III):

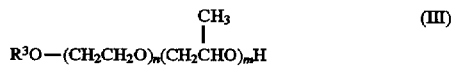

in which $R^3$ is an alkyl and/or alkenyl radical containing 6 to 22 and preferably 12 to 18 carbon atoms, n is 0 or a number of 1 to 20 and m is 0 or a number of 1 to 2.

Typical examples of suitable fatty alcohols are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol and erucyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols. Technical fatty alcohols containing 12 to 18 carbon atoms, such as for example cocofatty alcohol, palm oil fatty alcohol, palm kernel oil fatty alcohol or tallow fatty alcohol, are preferred.

Typical examples of fatty alcohol alkoxylates are adducts of 1 to 20 and preferably 2 to 10 moles of ethylene oxide and/or 1 to 2 moles of propylene oxide with the above-mentioned alcohols.

The alkoxylates may have both a conventional homolog distribution and a narrow homolog distribution.

Components (a) and (b) may be used in a molar ratio of 20:80 to 80:20, preferably in a molar ratio of 30:70 to 70:30 and more preferably in a molar ratio of 50:50 to 40:60.

Sulfation

The co-sulfation of the mixtures may be carried out in the manner known for fatty acid lower alkyl esters [J. Falbe (ed.), "Surfactants in Consumer Products", Springer Verlag, Berlin-Heidelberg, 1987, page 61], preferably using reactors operating on the falling-film principle. Chlorosulfonic acid and, more particularly, gaseous sulfur trioxide are used as sulfonating agents. The gaseous sulfur trioxide is normally diluted with an inert gas, preferably air or nitrogen, and used in the form of a gas mixture containing the sulfonating agent in a concentration of 1 to 8% by volume and, more particularly, 2 to 5% by volume.

The molar ratio of components (a)+(b) to the sulfating agent may be from 1:0.95 to 1:1.5 and is preferably from 1:1.0 to 1:1.2. The sulfation reaction is normally carried out at temperatures of 25° to 60° C. With regard to the viscosity of the starting materials on the one hand and the color quality of the resulting sulfation products on the other hand, it has been found to be optimal to carry out the reaction at a temperature in the range from 30° to 50° C.

Neutralization

The acidic sulfonation products obtained in the sulfation reaction are stirred into aqueous bases, neutralized and adjusted to a pH value of 6.5 to 8.5. Suitable bases for neutralization are alkali metal hydroxides, such as sodium, potassium and lithium hydroxide, alkaline earth metal oxides and hydroxides, such as magnesium oxide, magnesium hydroxide, calcium oxide and calcium hydroxide, ammonia, mono-, di- and tri-$C_{2-4}$-alkanolamines, for example mono-, di- and triethanolamine, and primary, secondary or tertiary $C_{1-4}$ alkylamines and glucamines. The neutralization bases are preferably used in the form of 5 to 55% by weight aqueous solutions, 5 to 25% by weight aqueous sodium hydroxide solutions being preferred.

Bleaching and Preservation

Although the sulfation products are unexpectedly light in color, they may be additionally bleached in known manner after neutralization by addition of hydrogen peroxide or sodium hypochlorite solution. Based on the solids content in the solution of the sulfation products, 0.2 to 2% by weight of hydrogen peroxide (expressed as 100% substance) or corresponding quantities of sodium hypochlorite are used. The pH value of the solutions may be kept constant using suitable buffers, for example sodium phosphate or citric acid. In addition, preservation, for example with formaldehyde solution, p-hydroxybenzoate, sorbic acid or other known preservatives, is advisable for stabilization against bacterial contamination.

Commercial Applications

The anionic detergent mixtures according to the invention are distinguished by particularly high foaming and cleaning power. Accordingly, the present invention also relates to their use for the production of surface-active compositions, for example laundry detergents, dishwashing detergents, cleaning products and softeners and also hair-care and personal-care products, in which they may be present in quantities of 1 to 50% by weight and preferably 2 to 30% by weight, based on the particular product.

Surface-active Formulations

Powder-form universal detergents containing 10 to 30% by weight—based on the detergent—of the artionic detergent mixtures according to the invention and typical auxiliaries and additives.

Liquid universal detergents containing 10 to 70% by weight—based on the detergent—of the anionic detergent mixtures according to the invention and typical auxiliaries and additives.

Liquid light-duty detergents containing 10 to 50% by weight—based on the detergent—of the anionic detergent mixtures according to the invention and typical auxiliaries and additives.

Softeners containing 10 to 50% by weight—based on the softener—of the anionic detergent mixtures according to the invention and typical auxiliaries and additives.

Manual dishwashing detergents containing 10 to 50% by weight—based on the detergent—of the anionic detergent mixtures according to the invention and typical auxiliaries and additives.

Rinse aids containing 10 to 50% by weight—based on the rinse aid—of the anionic detergent mixtures according to the invention and typical auxiliaries and additives.

Liquid cleaners and disinfectants containing 10 to 30% by weight—based on the cleaner/disinfectant—of the anionic detergent mixtures according to the invention and typical auxiliaries and additives.

Bar soaps of the so-called combibar type containing 1 to 2% by weight—based on the bar soap—of the anionic detergent mixtures according to the invention and typical auxiliaries and additives.

Syndet soaps containing 1 to 2% by weight—based on the soap—of the anionic detergent mixtures according to the invention and typical auxiliaries and additives.

Hair shampoos containing 10 to 30% by weight—based on the shampoo—of the anionic detergent mixtures according to the invention and typical auxiliaries and additives.

Hair rinses containing 10 to 30% by weight—based on the hair rinse—of the anionic detergent mixtures according to the invention and typical auxiliaries and additives.

Hair colorants containing 10 to 30% by weight—based on the hair colorant—of the anionic detergent mixtures according to the invention and typical auxiliaries and additives.

Hair waving formulations containing 10 to 30% by weight—based on the formulation—of the anionic detergent mixtures according to the invention and typical auxiliaries and additives.

Foam baths containing 10 to 30% by weight—based on the foam bath—of the anionic detergent mixtures according to the invention and typical auxiliaries and additives.

Textile and fiber auxiliaries containing 1 to 30% by weight—based on the auxiliary—of the anionic detergent mixtures according to the invention and typical auxiliaries and additives.

Leather oiling preparations containing 1 to 30% by weight—based on the preparation—of the anionic detergent mixtures according to the invention and typical auxiliaries and additives.

Flotation aids containing 1 to 30% by weight—based on the flotation—of the anionic detergent mixtures according to the invention and typical auxiliaries and additives.

Auxiliaries for dewatering solids containing 1 to 30% by weight—based on the auxiliary—of the anionic detergent mixtures according to the invention and typical auxiliaries and additives.

The following Examples are intended to illustrate the invention without limiting it in any way.

EXAMPLES

Example 1

Sulfation of a Glucamide/fatty Alcohol Mixture 460 g (1 mole) of lauric acid-N-methyl glucamide and 270 g (1 mole) of lauryl alcohol were introduced into and heated to 35° C. in a 1 liter sulfonation reactor with a gas inlet pipe and a jacket cooling system. 176 g (2.2 moles) of gaseous sulfur trioxide in the form of a 3% by volume gas mixture with nitrogen were introduced into the mixture over a period of 45 minutes. The acidic sulfation product was neutralized together with 25% by weight aqueous sodium hydroxide solution, buffered with 1% by weight of citric acid and adjusted to a pH value of 8.2. The characteristic data of the product are set out in Table 1 (percentages as % by weight).

Example 2

As in Example 1, 474 g (1 mole) of $C_{12/14}$ cocofatty acid-N-methyl glucamide and 340 g (1 mole) of $C_{16/18}$ tallow fatty alcohol were initially introduced and reacted at 50° C. with 184 g (2.5 moles) of sulfur trioxide. The characteristic data of the product are set out in Table 1.

Example 3

474 g of $C_{12/14}$ cocofatty acid-N-methyl glucamide and 358 g (1 mole) of lauryl alcohol+2EO were initially introduced as in Example 1 and reacted at 45° C. with 168 g (2.1 moles) of sulfur trioxide. The product was neutralized with glucamine. The characteristic data of the product are set out in Table 1.

Example 4

In a continuous sulfonation reactor (length 1 meter, diameter 0.8 cm) with a jacket cooling system, a continuous film of a mixture of $C_{12/14}$ cocofatty acid-N-methyl glucamide and $C_{12/14}$ cocofatty alcohol in a molar ratio of 1:1 was formed in a layer thickness of around 1 mm and reacted at 50° C. in the upper third with a 2% by volume gas mixture of $SO_3$ in air. The molar reaction ratio between the starting mixture and the $SO_3$ was adjusted to a value of around 1:1.5 through the addition rate of the starting materials. The crude sulfation product was continuously neutralized with 25% by weight aqueous sodium hydroxide solution, buffered with citric acid and adjusted to a pH value of 8.5. The characteristic data of the product are set out in Table 1.

TABLE 1

| | | | Sulfation tests | | | | |
|---|---|---|---|---|---|---|---|
| Ex. | E:SO₃ | T °C. | WAS % | US % | Salt % | H₂O % | Color Klett |
| 1 | 1:1:1 | 35 | 26.9 | 3.1 | 1.2 | 68.8 | 98 |
| 2 | 1:1.25 | 50 | 28.7 | 3.0 | 1.3 | 67.4 | 114 |
| 3 | 1:1.05 | 45 | 26.9 | 3.1 | 1.8 | 68.2 | 90 |
| 4 | 1:1.05 | 50 | 41.1 | 4.9 | 1.0 | 53.0 | 73 |

Legend:
E:SO₃ = Educt:SO₃ ratio
T = Temperature
WAS = Washing-active substance
US = Unsulfonated The quantity of anionic surfactant (WAS) and the content of unsulfonated substance (US) were determined in accordance with the DGF guidelines. The color of the unbleached pastes was determined in a Klett photometer (1 cm round cuvette, 5% WAS in isopropyl alcohol).

I claim:

1. A process for the production of anionic detergent compositions comprising reacting a mixture containing
   (a) fatty acid-N-alkyl polyhydroxyalkylamides and
   (b) fatty alcohols or fatty alcohol alkoxylates
with gaseous sulfur trioxide or chlorosulfonic acid in the absence of inert solvents, and neutralizing the reaction product obtained with a base.

2. The process according to claim 1 wherein said fatty acid-N-alkyl polyhydroxyalkylamides correspond to formula (I):

in which $R^1CO$ is an aliphatic acyl radical containing 6 to 22 carbon atoms, $R^2$ is hydrogen, an alkyl or hydroxyalkyl radical containing 1 to 4 carbon atoms and Z is a linear or branched polyhydroxyalkyl radical containing 3 to 12 carbon atoms and 3 to 10 hydroxyl groups.

3. The process according to claim 1 wherein said fatty alcohols or fatty alcohol alkoxylates correspond to formula (III):

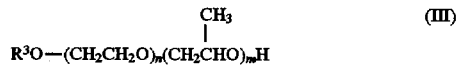

in which $R^3$ is an alkyl or alkenyl radical containing 6 to 22 carbon atoms, n is 0 or a number of 1 to 20 and m is 0 or a number of 1 to 2.

4. The process according to claim 1 wherein said components (a) and (b) are present in a molar ratio of 20:80 to 80:20.

5. The process according to claim 1 wherein the sulfation reaction is carried out with a molar ratio of the mixture of components (a)+(b) to sulfur trioxide or chlorosulfonic acid of 1:0.95 to 1:1.5.

6. The process according to claim 1 wherein the sulfation reaction is carried out at a temperature of 25° C. to 60° C.

7. The process according to claim 1 wherein the sulfation reaction is carried out in a continuous falling-film reactor.

8. The process according to claim 1 wherein said neutralizing step is carried out with a 5 to 55% by weight solution of a base selected from the group consisting of alkali metal hydroxides, alkaline earth metal oxides and hydroxides, ammonia, mono-, di- and tri-$C_{2-4}$-alkanolamines, and primary, secondary and tertiary $C_{1-4}$ alkylamines and glucamines.

9. Anionic detergent compositions produced by the process of reacting
   (a) fatty acid-N-alkyl polyhydroxyalkylamides and
   (b) fatty alcohols or fatty alcohol alkoxylates
with gaseous sulfur trioxide or chlorosulfonic acid in the absence of inert solvents, and then neutralizing the reaction product with a base.

10. Compositions according to claim 9 wherein said fatty acid-N-alkyl polyhydroxyalkylamides correspond to formula (I):

$$\begin{array}{c} R^2 \\ | \\ R^1CO-N-Z \end{array} \quad (I)$$

in which $R^1CO$ is an aliphatic acyl radical containing 6 to 22 carbon atoms, $R^2$ is hydrogen, an alkyl or hydroxyalkyl radical containing 1 to 4 carbon atoms and Z is a linear or branched polyhydroxyalkyl radical containing 3 to 12 carbon atoms and 3 to 10 hydroxyl groups.

11. Compositions according to claim 9 wherein said fatty alcohols or fatty alcohol alkoxylates correspond to formula (III):

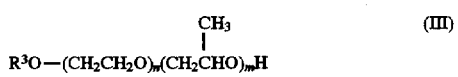

$$R^3O-(CH_2CH_2O)_n(CH_2CHO)_mH \quad (III)$$
with CH$_3$ branch in which $R^3$ is an alkyl or alkenyl radical containing 6 to 22 carbon atoms, n is 0 or a number of 1 to 20 and m is 0 or a number of 1 to 2.

12. Compositions according to claim 9 wherein said components (a) and (b) are present in a molar ratio of 20:80 to 80:20.

13. Compositions according to claim 9 wherein the sulfation reaction is carried out with a molar ratio of the mixture of components (a)+(b) to sulfur trioxide or chlorosulfonic acid of 1:0.95 to 1:1.5.

14. Compositions according to claim 9 wherein the sulfation reaction is carried out at a temperature of 25° C. to 60° C.

15. Compositions according to claim 9 wherein the sulfation reaction is carried out in a continuous falling-film reactor.

16. Compositions according to claim 9 wherein said neutralizing step is carried out with a 5 to 55% by weight solution of a base selected from the group consisting of alkali metal hydroxides, alkaline earth metal oxides and hydroxides, ammonia, mono-, di- and tri-$C_{2-4}$-alkanolamines, and primary, secondary and tertiary $C_{1-4}$ alkylamines and glucamines.

17. A surface-active composition comprising an anionic detergent mixture produced by the process of reacting a mixture containing
   (a) fatty acid-N-alkyl polyhydroxyalkylamides and
   (b) fatty alcohols or fatty alcohol alkoxylates
with gaseous sulfur trioxide or chlorosulfonic acid in the absence of inert solvents, and neutralizing the reaction product obtained with a base.

18. A composition according to claim 17 wherein said fatty acid-N-alkyl polyhydroxyalkylamides correspond to formula (I):

$$\begin{array}{c} R^2 \\ | \\ R^1CO-N-Z \end{array} \quad (I)$$

in which $R^1CO$ is an aliphatic acyl radical containing 6 to 22 carbon atoms, $R^2$ is hydrogen, an alkyl or hydroxyalkyl radical containing 1 to 4 carbon atoms and Z is a linear or branched polyhydroxyalkyl radical containing 3 to 12 carbon atoms and 3 to 10 hydroxyl groups.

19. A composition according to claim 17 wherein said fatty alcohols or fatty alcohol alkoxylates correspond to formula (III):

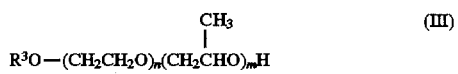

$$R^3O-(CH_2CH_2O)_n(CH_2CHO)_mH \quad (III)$$

in which $R^3$ is an alkyl or alkenyl radical containing 6 to 22 carbon atoms, n is 0 or a number of 1 to 20 and m is 0 or a number of 1 to 2.

20. A composition according to claim 17 wherein said components (a) and (b) are present in a molar ratio of 20:80 to 80:20.

* * * * *